United States Patent
Wallace et al.

(10) Patent No.: US 10,918,504 B2
(45) Date of Patent: Feb. 16, 2021

(54) VASCULAR IMPLANT

(71) Applicant: Silk Road Medical, Inc., Sunnyvale, CA (US)

(72) Inventors: Michael P. Wallace, Sunnyvale, CA (US); Herbert Mendoza, Sunnyvale, CA (US); Roy Leguidleguid, Sunnyvale, CA (US)

(73) Assignee: Silk Road Medical, Inc., Sunnyvale, CA (US)

( * ) Notice: Subject to any disclaimer, the term of this patent is extended or adjusted under 35 U.S.C. 154(b) by 15 days.

(21) Appl. No.: 15/901,502

(22) Filed: Feb. 21, 2018

(65) Prior Publication Data

US 2018/0235789 A1    Aug. 23, 2018

Related U.S. Application Data

(60) Provisional application No. 62/461,616, filed on Feb. 21, 2017.

(51) Int. Cl.
| | |
|---|---|
| *A61F 2/915* | (2013.01) |
| *A61F 2/86* | (2013.01) |
| *A61F 2/90* | (2013.01) |
| A61F 2/852 | (2013.01) |
| A61F 2/07 | (2013.01) |

(52) U.S. Cl.
CPC .............. *A61F 2/915* (2013.01); *A61F 2/86* (2013.01); *A61F 2/90* (2013.01); *A61F 2/07* (2013.01); *A61F 2/852* (2013.01); *A61F 2002/9155* (2013.01); *A61F 2002/91566* (2013.01); *A61F 2002/91575* (2013.01); *A61F 2210/0076* (2013.01)

(58) Field of Classification Search
CPC .... A61F 2/915; A61F 2/90; A61F 2/86; A61F 2002/91575; A61F 2/07; A61F 2210/0076; A61F 2/852; A61F 2002/91566; A61F 2002/9155
See application file for complete search history.

(56) References Cited

U.S. PATENT DOCUMENTS

| | | |
|---|---|---|
| 4,580,568 A | 4/1986 | Gianturco |
| 4,733,665 A | 3/1988 | Palmaz |

(Continued)

FOREIGN PATENT DOCUMENTS

EP    2151217 A1    2/2010

OTHER PUBLICATIONS

Henry et al. (1999) "Carotid stenting with cerebral protection: First clinical experience using the PercuSurge GuardWire System" J. Endovasc. Surg. 6:321-331.

*Primary Examiner* — Ryan J. Walters
(74) *Attorney, Agent, or Firm* — Mintz Levin Cohn Ferris Glovsky and Popeo, P.C.

(57) ABSTRACT

Methods and devices relate to the use and construction of a vascular stent. A stent assembly includes mesh structure that is at least partially attached to a support or stent structure. The stent structure is formed of one or more struts that collectively form a tubular body sized to fit within a blood vessel. The mesh structure is formed of one or more filaments or sutures that are interwoven or knit to form a structure that is coupled to the stent structure. The mesh structure can at least partially cover or at least be partially covered by the stent structure.

7 Claims, 9 Drawing Sheets

(56) References Cited

U.S. PATENT DOCUMENTS

| | | | |
|---|---|---|---|
| 5,667,523 A | 9/1997 | Bynon et al. | |
| 5,735,897 A * | 4/1998 | Buirge | A61F 2/82 623/1.15 |
| 5,755,770 A | 5/1998 | Ravenscroft | |
| 6,287,333 B1 * | 9/2001 | Appling | A61F 2/88 623/1.15 |
| 6,296,661 B1 | 10/2001 | Davila et al. | |
| 6,413,235 B1 | 7/2002 | Parodi | |
| 6,423,032 B2 | 7/2002 | Parodi | |
| 6,595,953 B1 | 7/2003 | Coppi et al. | |
| 6,613,078 B1 * | 9/2003 | Barone | A61F 2/07 606/194 |
| 6,837,881 B1 | 1/2005 | Barbut | |
| 7,083,594 B2 | 8/2006 | Coppi | |
| 7,300,459 B2 * | 11/2007 | Heuser | A61F 2/07 623/1.34 |
| 9,126,018 B1 | 9/2015 | Garrison | |
| 9,241,699 B1 | 1/2016 | Kume et al. | |
| 10,039,906 B2 | 8/2018 | Kume et al. | |
| 10,085,864 B2 | 10/2018 | Chou et al. | |
| 10,159,479 B2 | 12/2018 | Hentges et al. | |
| 2001/0044598 A1 | 11/2001 | Parodi | |
| 2003/0009211 A1 | 1/2003 | DiCarlo | |
| 2005/0154344 A1 | 7/2005 | Chang | |
| 2005/0154349 A1 | 7/2005 | Renz et al. | |
| 2006/0106338 A1 | 5/2006 | Chang | |
| 2009/0018455 A1 | 1/2009 | Chang | |
| 2009/0024072 A1 | 1/2009 | Criado et al. | |
| 2009/0198172 A1 | 8/2009 | Garrison et al. | |
| 2009/0254166 A1 | 10/2009 | Chou et al. | |
| 2009/0306755 A1 | 12/2009 | Dickinson et al. | |
| 2010/0042118 A1 | 2/2010 | Garrison et al. | |
| 2010/0185216 A1 | 7/2010 | Garrison et al. | |
| 2010/0191169 A1 | 7/2010 | Chang | |
| 2010/0191170 A1 | 7/2010 | Chang | |
| 2010/0204684 A1 | 8/2010 | Garrison et al. | |
| 2010/0217276 A1 | 8/2010 | Garrison et al. | |
| 2010/0228269 A1 | 9/2010 | Garrison et al. | |
| 2010/0280431 A1 | 11/2010 | Criado et al. | |
| 2011/0004147 A1 | 1/2011 | Renati et al. | |
| 2011/0034986 A1 | 2/2011 | Chou et al. | |
| 2011/0082408 A1 | 4/2011 | Chang | |
| 2011/0087147 A1 | 4/2011 | Garrison et al. | |
| 2011/0125131 A1 | 5/2011 | Chang | |
| 2011/0166496 A1 | 7/2011 | Criado et al. | |
| 2011/0166497 A1 | 7/2011 | Criado et al. | |
| 2011/0208067 A1 * | 8/2011 | Edman | A61B 5/0295 600/486 |
| 2011/0213459 A1 | 9/2011 | Garrison et al. | |
| 2013/0172852 A1 | 7/2013 | Chang | |
| 2013/0197621 A1 | 8/2013 | Ryan et al. | |
| 2014/0031682 A1 | 1/2014 | Renati et al. | |
| 2014/0031925 A1 | 1/2014 | Garrison et al. | |
| 2014/0046346 A1 | 2/2014 | Hentges et al. | |
| 2014/0058414 A1 | 2/2014 | Garrison et al. | |
| 2014/0135661 A1 | 5/2014 | Garrison et al. | |
| 2014/0296769 A1 | 10/2014 | Hyde et al. | |
| 2014/0296868 A1 | 10/2014 | Garrison et al. | |
| 2014/0343676 A1 | 11/2014 | Woodroof | |
| 2014/0371653 A1 | 12/2014 | Criado et al. | |
| 2015/0025616 A1 | 1/2015 | Chang | |
| 2015/0080942 A1 | 3/2015 | Garrison et al. | |
| 2015/0141760 A1 | 5/2015 | Chou et al. | |
| 2015/0150562 A1 | 6/2015 | Chang | |
| 2015/0174368 A1 | 6/2015 | Garrison et al. | |
| 2015/0327843 A1 | 11/2015 | Garrison | |
| 2016/0128688 A1 | 5/2016 | Garrison et al. | |
| 2016/0158044 A1 | 6/2016 | Chou et al. | |
| 2016/0158502 A1 | 6/2016 | Kume et al. | |
| 2016/0166804 A1 | 6/2016 | Garrison et al. | |
| 2016/0242764 A1 | 8/2016 | Garrison et al. | |
| 2016/0271315 A1 | 9/2016 | Chang | |
| 2016/0271316 A1 | 9/2016 | Criado et al. | |
| 2016/0279379 A1 | 9/2016 | Chang | |
| 2016/0296690 A1 | 10/2016 | Kume et al. | |
| 2016/0317288 A1 | 11/2016 | Rogers et al. | |
| 2017/0043141 A1 | 2/2017 | Kume et al. | |
| 2017/0136212 A1 | 5/2017 | Garrison et al. | |
| 2017/0209260 A1 | 7/2017 | Garrison et al. | |
| 2017/0296798 A1 | 10/2017 | Kume et al. | |
| 2017/0312491 A1 | 11/2017 | Ryan et al. | |
| 2017/0354523 A1 | 12/2017 | Chou et al. | |
| 2017/0354803 A1 | 12/2017 | Kume et al. | |
| 2017/0361072 A1 | 12/2017 | Chou et al. | |
| 2017/0368296 A1 | 12/2017 | Chang | |
| 2018/0008294 A1 | 1/2018 | Garrison et al. | |
| 2018/0154063 A1 | 6/2018 | Criado et al. | |
| 2018/0185614 A1 | 7/2018 | Garrison et al. | |
| 2018/0289884 A1 | 10/2018 | Criado et al. | |
| 2019/0105439 A1 | 4/2019 | Criado et al. | |
| 2019/0125512 A1 | 5/2019 | MacDonald et al. | |
| 2019/0150916 A1 | 5/2019 | Hentges et al. | |
| 2019/0175885 A1 | 6/2019 | Kume et al. | |
| 2019/0231962 A1 | 8/2019 | Criado et al. | |
| 2019/0254680 A1 | 8/2019 | Chang | |
| 2019/0262530 A1 | 8/2019 | Criado et al. | |
| 2019/0269538 A1 | 9/2019 | Chou et al. | |
| 2019/0350568 A1 | 11/2019 | Garrison | |
| 2019/0366070 A1 | 12/2019 | Kume et al. | |
| 2019/0388654 A1 | 12/2019 | Chou et al. | |
| 2020/0009406 A1 | 1/2020 | Garrison et al. | |
| 2020/0015826 A1 | 1/2020 | Chang | |
| 2020/0016321 A1 | 1/2020 | Criado et al. | |

* cited by examiner

VASCULAR IMPLANT

CROSS REFERENCE TO RELATED APPLICATIONS

The present application claims priority under 35 U.S.C. § 119 to U.S. Provisional Application No. 62/461,616 filed Feb. 21, 2017, the disclosure of which is incorporated herein by reference. The provisional application is incorporated by reference in its entirety.

BACKGROUND

Stents for transluminal implantation are generally made of metallic supports that are inserted into a part of the human body such as inside a blood vessel. Stents are usually generally cylindrical and are constructed and arranged to expand radially once in position within the body. Some stents include a graft or mesh structure that can be used to minimize or eliminate the risk of disease herniating through a body-implanted stent during a healing phase.

The mesh structure of a stent assembly can add to the overall width of the stent, which can be undesirable. It is therefore desirable to manufacture a stent such that the mechanical attachment between the mesh structure and stent structure is efficient from a size standpoint. It also is important that the mesh structure be properly and securely attached to the support portion of the stent.

SUMMARY

Disclosed herein are methods and devices related to the use and construction of a vascular stent assembly. A stent assembly includes a mesh structure that is positioned over and/or at least partially attached to a stent structure. Also disclosed are devices and methods for securely attaching the mesh structure to the stent structure. The stent assembly can also include or be coupled with a stent delivery system that is configured to deliver the stent assembly into a blood vessel of a patient.

In one aspect, there is disclosed a stent assembly adapted to be implanted in a blood vessel, comprising: an inner stent structure formed of a plurality of interconnected struts; an outer stent structure formed of a plurality of interconnected struts, the inner stent structure positioned within the outer stent structure to form a space therebetween, wherein the inner stent structure and outer stent structure collectively form a stent body sized and shaped to fit within a blood vessel; and a mesh structure positioned at least partially in the space between the inner stent structure and outer stent structure such that the mesh structure is attached to the inner stent structure and outer stent structure in a sandwich arrangement.

In another aspect, there is disclosed a method of forming a stent assembly comprising: forming an inner stent structure of a plurality of interconnected struts; forming an outer stent structure of a plurality of interconnected struts; positioning the inner stent structure within the outer stent structure to form a space therebetween, wherein the inner stent structure and outer stent structure collectively form a stent body sized and shaped to fit within a blood vessel; positioning a mesh structure at least partially in the space between the inner stent structure and outer stent structure; and sandwiching the mesh structure in the space between the inner stent structure and outer stent structure to attached the mesh structure to the inner stent structure and outer stent structure.

Other features and advantages should be apparent from the following description of various embodiments, which illustrate, by way of example, the principles of the disclosure.

DETAILED DESCRIPTION

Disclosed herein are methods and devices related to the use and construction of a vascular stent. A stent assembly includes mesh structure that is positioned over and/or at least partially attached to a support or stent structure. The stent structure is formed of one or more struts that collectively form a tubular body sized to fit within a blood vessel. The mesh structure is formed of one or more filaments or sutures that are interwoven or knit to form a structure that is coupled to the stent structure pursuant to any of the configurations described herein. The mesh structure can at least partially cover or at least be partially covered by the stent structure.

The stent assembly can also include or be coupled with a stent delivery system that is configured to deliver the stent assembly into a blood vessel of a patient. An example stent delivery system includes an elongated stent delivery catheter that can be inserted into a blood vessel such as in a percutaneous manner. The stent assembly can be mounted on the stent delivery catheter such as on a distal region of the stent delivery catheter. The stent delivery catheter can then be deployed to a target site and the stent assembly can be released from the stent delivery catheter so that the stent assembly deploys and is retained in target location in the blood vessel.

The stent assembly can be used for implanting in any blood vessel including the carotid artery. The mesh structure of the stent assembly can be used to minimize or eliminate the risk of disease herniating through the stent during a healing phase in which the stent assembly is implanted in a patient, such as during the first 30 days of implantation.

The stent assembly can be any stent, including a self-expanding stent, or a stent that is radially expandable by inflating a balloon or expanded by an expansion member. The stent can also be made of any desired material, including a metallic material, a metal alloy (e.g., nickel-titanium)

or even polymeric composites. The stent can have any wire or cell design. The vessels in which the stent of the present invention can be deployed include but are not limited to natural body vessels such as a blood vessel.

Various examples of mesh configurations for coupling to a stent structure are described herein. The mesh configurations can include, for example, (1) material of the mesh; (2) thread configurations of the mesh; (3) size and quantity of filaments that form the mesh; (4) modes of attachment between the mesh and the stent, etc., and combinations thereof. Various embodiments of the stent structure for attaching to the mesh structure are also described herein.

Figure 1:
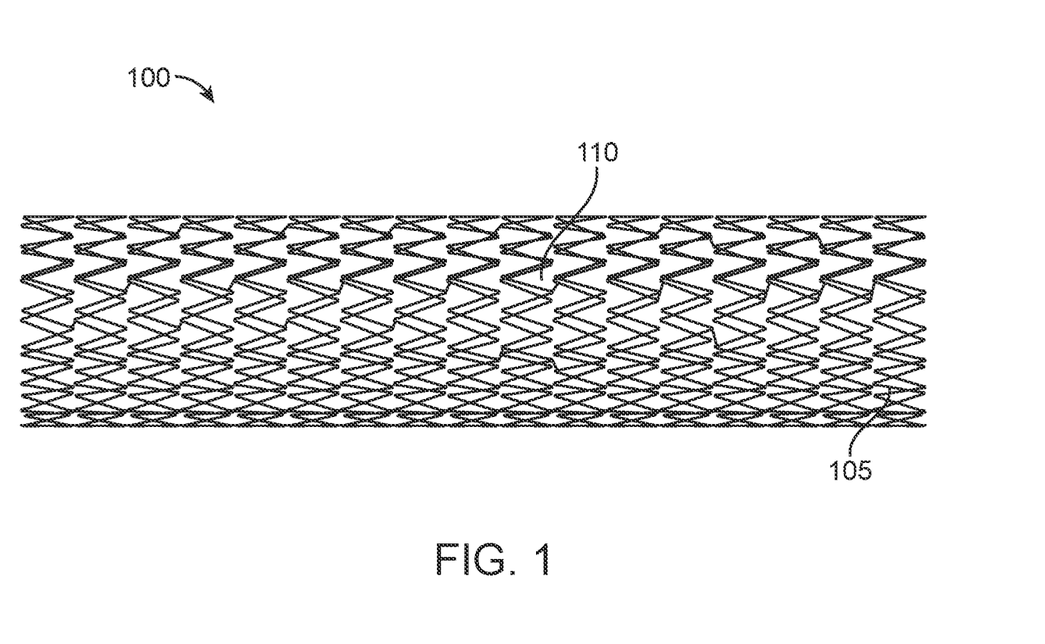
FIG. 1 shows an example stent assembly.

FIG. 1 shows a perspective view of a stent assembly 100 that includes a stent body 105 (or stent structure) that is coupled to a mesh body 110 (or mesh structure). The stent body is a formed of a plurality of interconnected struts or wires that are attached to one another to form a plurality of cells or openings. The struts can be attached to one another in any of a variety of manners. The stent body generally forms a cylindrical shape that is sized and shaped to fit within a blood vessel, such as a carotid artery.

In an embodiment, the mesh structure (sometimes referred to as "knit") is made of a shape memory alloy, such as Nickel Titanium (NiTi or Nitinol). In an example embodiment, the mesh structure formed of a 0.0005 inch nitinol filament positioned over the stent. In another example embodiment, the mesh structure is formed of a polyester monofilament or multifilament.

A stent with a Polyethylene terephthalate ("PET") mesh structure can be crimped down on to the stent structure for loading onto a delivery system. The mesh structure has a wall thickness such that it does not increase or significantly increase the overall thickness of the entire stent assembly. In this regard, the mesh structure may be dimensioned such that it has a wall thickness that is less than double the wall thickness of the stent structure.

There are now described various structures and methods for attaching the mesh structure to the stent structure.

Attachment Via Glue

Figure 2:
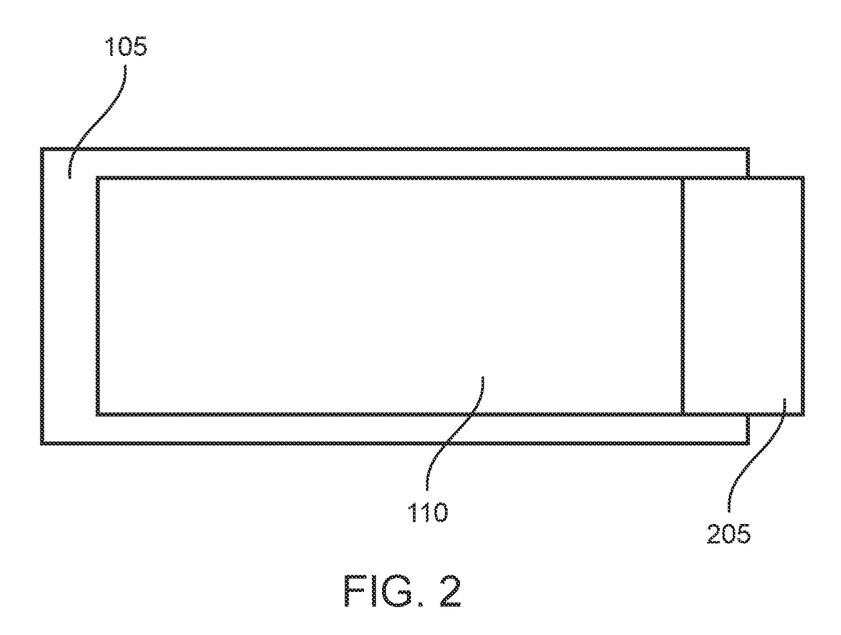
FIG. 2 shows a schematic representation of a hem structure that is used to attach a mesh structure to a stent structure.

In an embodiment for attaching the mesh structure 110 to the stent structure 105, a hem is formed and is used as a mechanical interface between the mesh structure 110 and the stent structure 105. For example, a planar portion of the material that is used to form the mesh structure is turned over itself to form such a hem. The hem defines a space in which a corresponding portion of the stent structure 105 can be inserted and secured. FIG. 2 shows a schematic representation of the hem structure 205, which is attached to the mesh structure 110 and to the stent structure 105.

Figure 3:
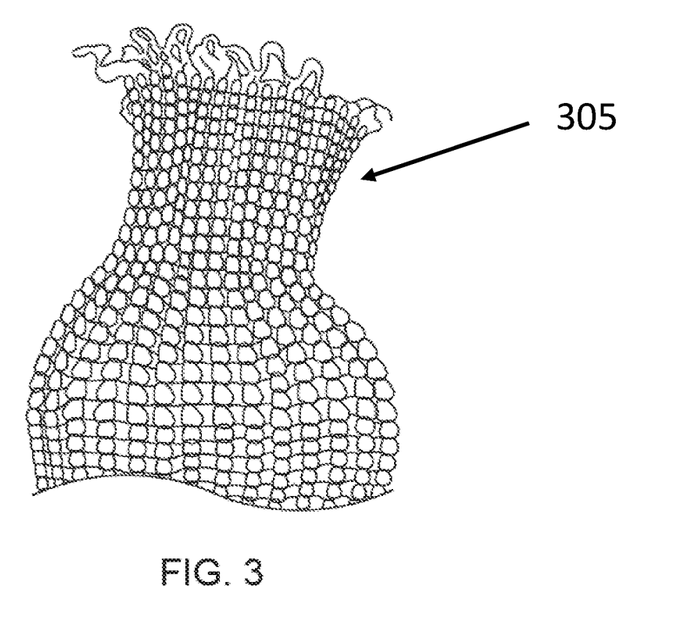
FIG. 3 shows an example wherein a meltable polymer leader is attached to a Nickel Titanium (NiTi) mesh structure.

The separate hem structure 205 is attached to the mesh structure 110 such as via sewing or gluing. Then the mesh structure 110 is glued to the stent structure 105 via any of a variety of methods. For example, the mesh structure can be soldered to the stent structure such as by gold soldering a NiTi mesh structure to the stent structure. Alternatively, a polymer glue, a melt, a solvent polymer bond, etc. or a conformal polymer coating can be used. FIG. 3 shows some examples of this wherein a meltable polymer leader 305 is attached to an NiTi mesh structure 110. The attached polymer portion of the mesh structure is then melted, bonded, or otherwise mechanically attached to the stent structure.

In this manner, the stent assembly includes a transition from a shape memory material, such as Nitinol, to a polymer material at an end of the stent assembly.

Mechanical Attachment Via Sandwiching

In another embodiment for attaching the mesh structure 110 to the stent structure 105, the mesh structure 110 is sandwiched between an inner stent structure 105a and an outer stent structure 105b. That is, the stent assembly includes two stent structures including an inner stent structure 105a and an outer stent structure 105b, as shown schematically in FIG. 4. The stent structures 105a and 105b form a space therebetween in which the mesh structure 110 can be at least partially positioned. In this manner, the mesh structure 110 is interposed or sandwiched between the stent structures 105a and 105b to form a secure attachment therebetween.

Figure 4:
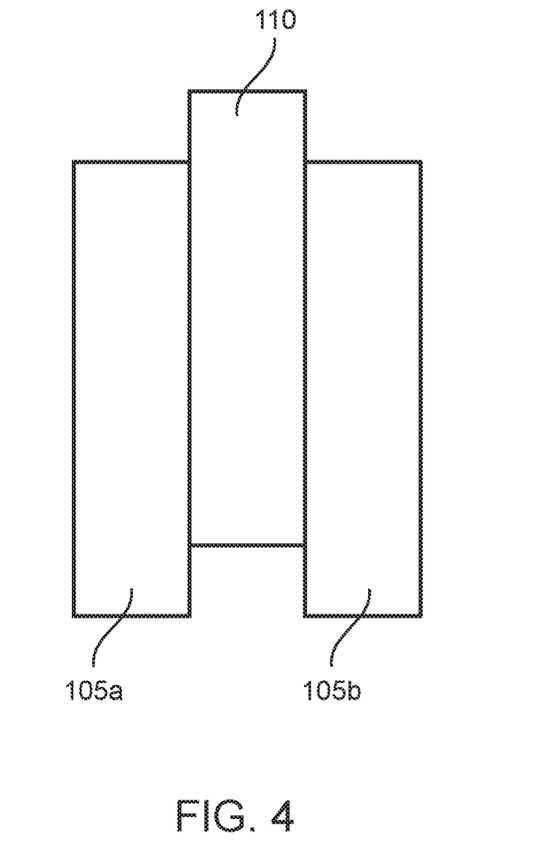
FIG. 4 shows a schematic representation of a stent assembly that includes two stent structures including an inner stent structure and an outer stent structure that form a space therebetween in which the mesh structure can be positioned and attached.

In an example, the following specifications can be used for the inner stent structure and outer stent structure:

A 0.003" outer stent structure over a NiTi mesh structure and a 0.006" inner stent structure;

A 0.002" outer stent structure over a NiTi mesh structure and a 0.008" or 0.009" inner stent structure.

Figure 5:
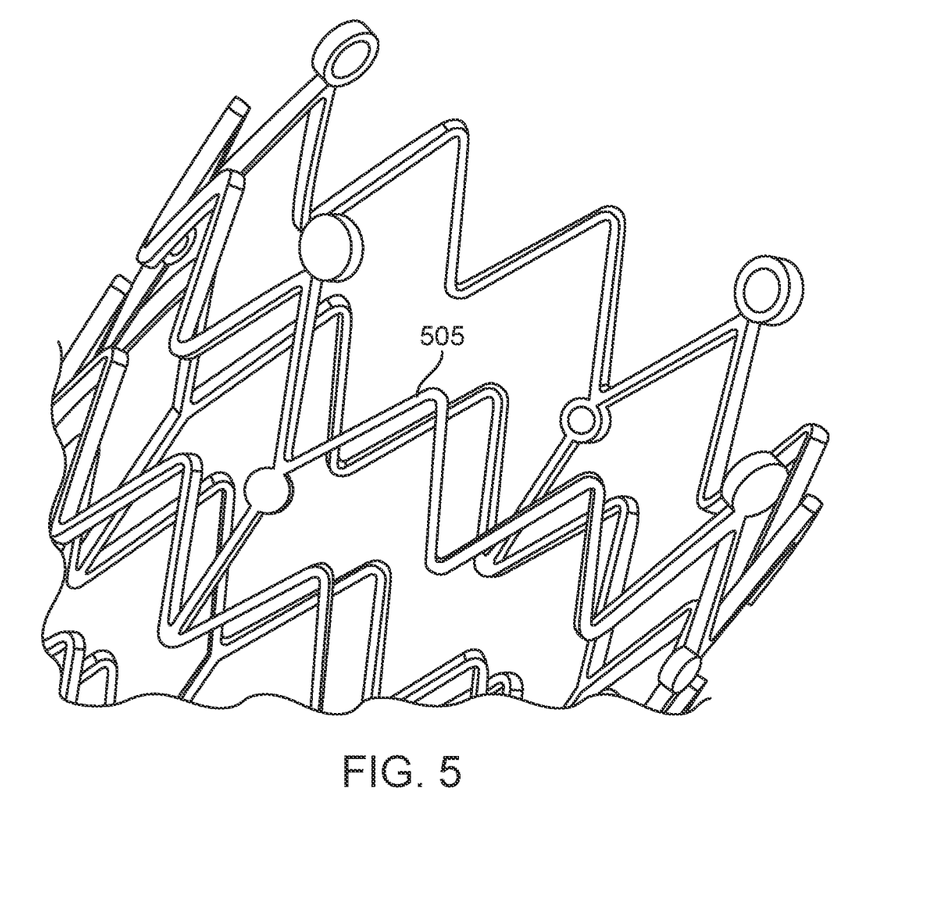
FIG. 5 shows an embodiment wherein a separate sandwiching retainer element is attached to a stent structure.

As shown in FIG. 5, in another sandwich embodiment, a separate sandwiching retainer element 505 is added on crown ends of the stent structure only. The mesh structure is not shown in FIG. 5.

The sandwich embodiments are now described further. An inner stent structure and an outer stent structure can encapsulate a mesh structure by placing the mesh structure therebetween. The inner stent structure exerts higher radial strength or radially outward force than the outer stent structure such that a net resulting force between the inner and outer stent structures pushes the entire stent assembly devices toward a blood vessel wall (e.g., radially outward) when implanted. Length-wise, both the inner stent structure and outer stent structure are longer than the length of the mesh structure. In an embodiment, both the inner stent structure and outer stent structure have identical specifications except two parameters. The first parameter is of strut length (SL) for the struts of the stent structure. The second parameter is a wall thickness (wt) of the stent structure.

In an example, the SL of the inner stent structure about 15% shorter and the SL of outer stent structure is about 15% longer. That is, all of the strut lengths of the inner stent structure are smaller than the shortest strut of the outer stent structure. The net difference in SL is 30% between inner stent structure and outer stent structure. By having shorter SL, the radial strength becomes higher. By having longer SL, the radial strength becomes lower. Thus, the radial strength of the entire stent assembly device exerts its radial strength outward (i.e., toward the blood vessel wall).

The wt of the inner stent structure is 0.006" and the wt of outer stent structure is 0.003". By having thinner wt, the radial strength becomes lower. By having thicker wt, the radial strength becomes higher. Thus, the radial strength of the composite device exerts its radial strength outward (e.g., toward the vessel wall direction). Also the net wt of the composite device is at or below a 0.009" threshold wt. By having both wt and SL tailored for either higher or lower radial strength for both inner and outer stents, respectively, the net radial strength of the composite device exerts outward force toward the vessel wall.

Attachment Via Machine Sewing

As mentioned, a hem can be formed on the mesh structure. The mesh can be formed using a sewing machine and the hem is attached to the stent structure. The mesh structure can also be machine sewed directly onto the struts of the stent structure. Pursuant to such a process, a filament is used to form a stitch pattern that attaches the mesh structure to the stent structure. The sewing stitch pattern can be formed from any variety of filaments including, for example, 205 hand stitch and 301 lock stitch. The stitching can be formed along struts of the stent (or just across struts of the stent) in a circumferential orientation. The stitch width can be constant or vary around the device's circumference.

The stitch can have a constant or a variable stitch length. For example, the stitch can be tighter at a certain number of discrete locations along the stent structure and less tight at remaining locations. The knit structure can also form pores of various shapes and sizes.

Attachment Via Hand Sewing

In another embodiment, the mesh structure is attached to the stent structure by hand sewing ends of the mesh structure to itself and/or to the stent. Preferred sewing patterns can be used with custom features on stent to make it easier to attach a suture onto the stent. Example sewing patterns include test 301 lock stitch and 205 hand stitch.

Figure 6:
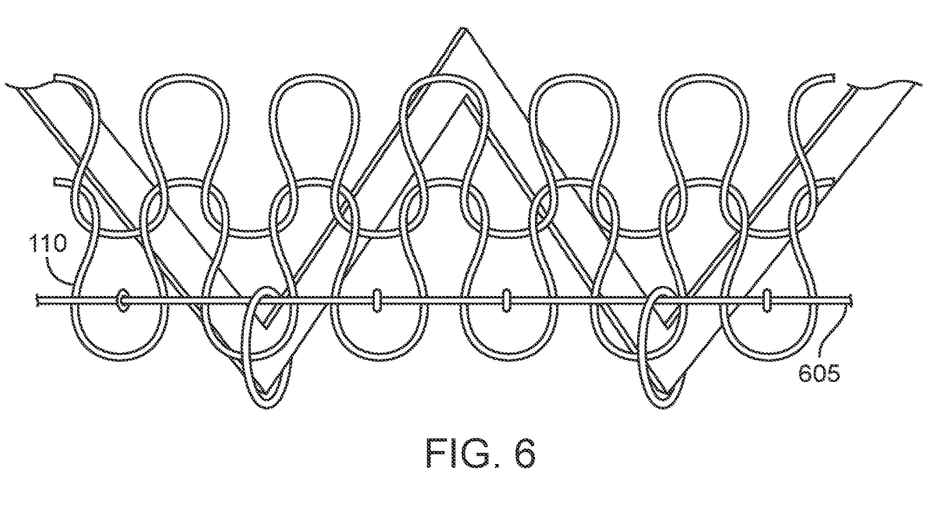
FIG. 6 shows an example of a filament being hand sewn through the end of a mesh structure.

FIG. 6 shows an example of a filament 605 being hand sewn through the end of the mesh structure 110. Individual loops of suture are then used to attach the mesh structure to the crowns of the stent structure. The filament is sewed so that it runs in and out of the loops. The quantity of loops may vary. In an embodiment, there are 10 to 100 loops.

In an embodiment, a filament (such as a PET filament) is sewn through the end of a NiTi mesh structure and connected to the stent structure. The filament is sewn through one or more loops of the mesh structure and also through donut holes or apertures along the crown of the stent structure.

Attachment Via Hand Sewing with Suture Anchors

A crown region of the stent assembly can include one or more types of suture anchors. The crown of the stent includes a first type of suture anchor with a "split O" configuration in which the suture anchor forms a partial loop with a gap or opening along its circumference. The gap or opening provides a passage for the suture to be inserted into the anchor.

Figure 7:
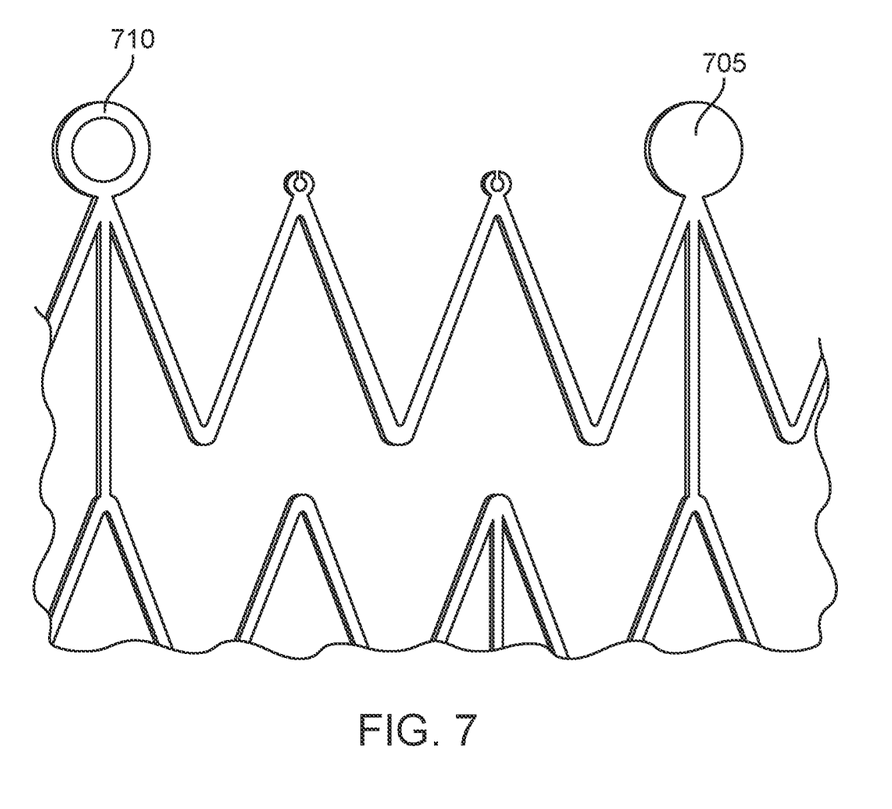
FIG. 7 shows an enlarged view of a crown region of a stent structure having a closed loop anchor and an open loop anchor.

The second type of suture anchor is a "solid circle" or closed loop in which the suture anchor forms a completely closed loop. FIG. 7 shows an enlarged view of the crown region of a stent structure having a closed loop anchor 705 and an open loop anchor 710. The suture can be looped through the open loop anchor and secured in a cleat manner, wherein the suture also extends through the open loop anchor. The suture can alternately be looped around the closed loop anchor and also be wrapped around a base of the anchor to further secure the suture thereto.

The mesh structure is desirably secured to the stent structure in a manner that will secure the mesh structure to the stent structure against forces applied in both a distal direction and a proximal direction along a longitudinal axis of the stent structure. That is, the mesh structure will remain secured and not detach from the stent structure regardless of a direction of relative force between the stent structure and the mesh structure.

Figure 8:
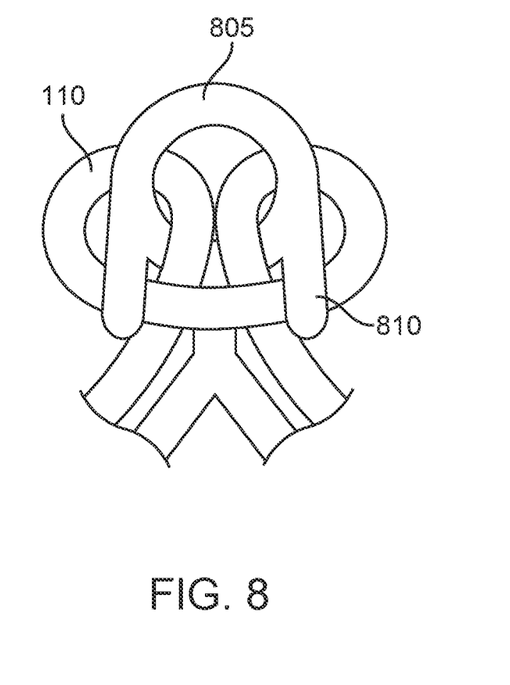
FIG. 8 shows an embodiment of an anchor that can be located on a crown of the stent structure.

FIG. 8 shows an embodiment of an anchor 805 that can be located on a crown of the stent structure. The anchor forms a closed loop and includes one or more "ears", prongs, barbs, or protrusions 810 that serve as structure for further securing the suture to the anchor. As shown in FIG. 8, the suture 805 can wrap through the closed loop and also around the ears to secure the suture thereto and prevent it from disengaging from the stent structure during loading and/or removal of the stent assembly from a delivery system. It should be appreciated that the ear structures are just examples and that other structures can be used to further secure the suture to the stent structure.

Mechanical Attachment Via Interconnecting Features

In another embodiment, the mesh mechanically interconnects with features of the stent. Various methods can be used to mechanically attach the mesh structure to the stent structure. For example, the end of the mesh structure can be looped over the end of the stent structure or the mesh structure is looped inside itself with both layers of the knit on the outside of the stent. The two knit layers can then be bonded or sutured together with this construct.

Alternatively, the end of the knit can be "finished" so that the filament used for the knitting does not unwind or unknit. The end of the knit is secured with any of the methods described in this disclosure. Next, the ends of the mesh structure are looped over some features of the stent. These features may include the crowns of the stent or finger-like protrusion structure. The protrusions may be directed away or outwardly to help the mesh structure to more easily engage.

Attachment Via Polymer Coating

In another embodiment, a polymer coating can be used to finish the ends of the mesh structure and/or attach the mesh structure to the stent structure. A thin layer of polymer is added on the end of the mesh structure to prevent the mesh structure from unraveling before attaching to the stent structure.

Alternately, a polymer coating is used to both help "finish" the end of the mesh structure and also act as a mechanism to attach mesh stent struts all at one time. For this example, the polymer can be sprayed on just the ends of the stent assembly thereby leaving the center of the stent/mesh structure clear of any polymer. The polymer coating can be applied to one or more rows of knit elements, less than one row of knit element, one or more strut rung element, or less than one strut rung element. To coat just the end of the knit, it may be required to mask the center of the stent structure with a masking agent that can be removed after the coating process is complete.

The polymer coating can be achieved with a dip or spray process with various levels of solids. Multiple passes may be required to get adequate coating. The key will be to encapsulate the entire knit filament-stent strut element with the coating to ensure it is adequately attached.

A variety of polymer gluing or coating options to secure mesh end and/or bond to stent are shown in table below.

| Stent | Company | Polymers | Reference |
|---|---|---|---|
| Cypher | Cordis | Parylene C primer Blend of: Polyethylenevinyl acetate (PEVA); Polybutylmethacrylate (PBMA) | Cypher IFU (2003) Cordis |
| Taxus | Boston Scientific | Poly(styrene-isobutylene-styrene) SIBS | Taxus Express2 IFU (2012) Boston Scientific |
| Endeavor | Medtronic | Phosphorocholine (PC) | EuroInterv (2007) 3: 137-139 |
| Endeavor Resolute | Metronic | Blend of: Polyvinylpyrrolidone (PVP); Poly(butyl-methacrylate/vinyl acetate) (C10); Poly(vinylacetate/vinylpyrrolidone/hexamethacrylate) (C19) | J Biomed Mater Res (2008) 85A: 1064-1071 |
| Xience | Guidant/Abbott | Copolymer of Poly(vinyidene fluoride - hexafloropropylene) | Cath Cardiovasc Inter (2006) 68: 97-103 |
| Other | Misc | PET, Pebax, Silicone, Urethanes, parylene m and/or C with or without functional groups, biomer | |

Other materials that can be used include, for example:

Parylene C: Conformal coating formed by vapor deposition. Long history with medical devices.

PEVA: Rubbery copolymer. Available in broad range of vinyl acetate ranges. Very low VA content (less than 10%) is difficult to dissolve. Higher VA (18-33%) would be very flexible and adhesive PBMA: Hard, tough material. Not as flexible as PEVA. Easily dissolvable in several solvents.

SIBS: Tough, rubbery material. Dissolvable in several solvents.

PC: Tends to form as a self-assembled monolayer.

PVP: Water soluble polymer.

Polyvinylidenefluroide/hexafluoropropylene Melt processible.

Attachment Via Welding

In another embodiment, the mesh structure can also be welded to the stent structure. For example, the following materials can be used in the weld process:

Niti wire (from Knit) to Niti stent weld: Laser welding, resistance welding

Polymer filament (from Knit) to Niti stent weld

Various mesh constructions can be used. A circular knitting method can be used wherein the pore size can be formed from any one of more polymer or metallic fiber or combinations there of. Example NiTi or PET fibers are about 0.001", 0.00075", 0.0005" diameter wires.

Exemplary Cell Pattern for Mesh or Stent Structure

Figure 9:
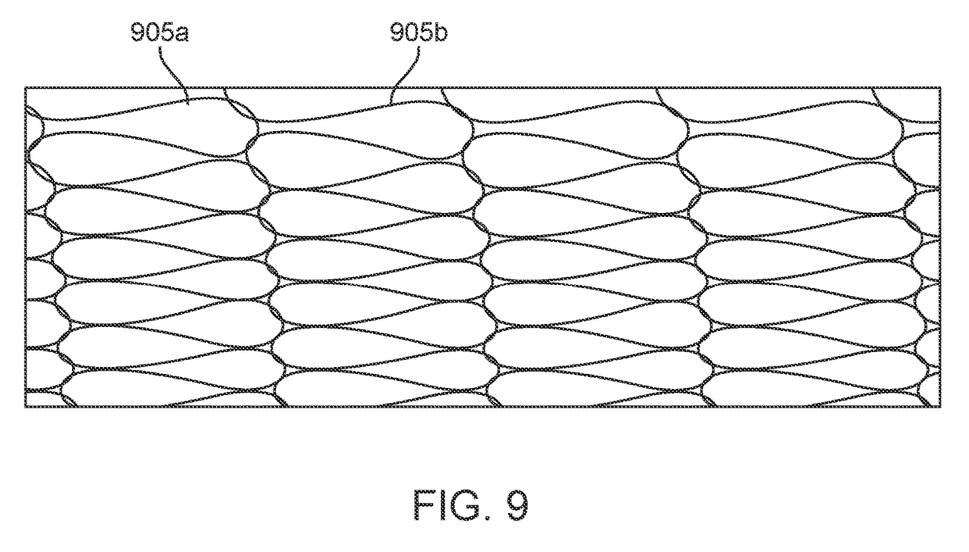
FIG. 9 shows an example stent assembly with tear drop shaped pores.

In an embodiment shown in FIG. 9, the knit or mesh structure can be formed and/or post processed to form a kissing pore or cell pattern. For example, the mesh structure forms a plurality of tear drop shaped pores 905 with enlarged rounded regions on a first end and smaller, pointed regions on a second end. In the kissing pattern, the enlarged rounded regions of at least two of the tear drop shaped pores are in contact or abut with one another. A tear drop shaped pore can extend along a long axis with the rounded region of a pore being positioned along the axis at a first end and the pointed region positioned along the axis on a second end, wherein the axis is straight. The pores can be arranged in rows such that the larger regions of two pores are in direct contact in "kissing" arrangement while the smaller regions of the two pores are spaced apart from one another. A series of pores (such as pores 905a and 905b) are co-axial along a common long axis. One way this pattern can be achieved is to knit a tubular knit structure with individual pores wherein at least some of the pores are generally circular, square or rectangular in shape. The tubular knit can be stretched longitudinally onto a smaller diameter mandrel to yield elongated pores which exhibit the kissing or tear drop shaped pattern; the structure may then be optionally heat set to retain this shape.

The above-described, tear drop shaped pore arrangement can achieve smaller pore sizes using particular wires to form the stent assembly and pores, such as Nitinol wire in the 0.0005" to 0.001" diameter range. The "kissing" pore configuration can achieved minimum pore widths of 100-250 um and a Length:Width ratio ranging from 3:1 to 10:1 in an example embodiment.

While this specification contains many specifics, these should not be construed as limitations on the scope of an invention that is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed.

The invention claimed is:

1. A method of forming a stent assembly comprising:
   forming an inner stent structure of a plurality of interconnected struts;
   forming an outer stent structure of a plurality of interconnected struts;
   positioning the inner stent structure within the outer stent structure to form a space therebetween, wherein the inner stent structure and outer stent structure collectively form a stent body sized and shaped to fit within a blood vessel;
   forming a tubular knit structure having a plurality of pores wherein at least some of the pores are circular, square or rectangular in shape;
   stretching the tubular knit structure longitudinally onto a mandrel to form the at least some of the pores into tear drop shaped pores;
   heat setting the tubular knot structure to form a mesh structure;
   positioning the mesh structure at least partially in the space between the inner stent structure and outer stent structure;
   sandwiching the mesh structure in the space between the inner stent structure and outer stent structure to attach the mesh structure to the inner stent structure and outer stent structure.

2. The method of claim 1, further comprising forming a hem on the mesh structure.

3. The method of claim 2, further comprising positioning at least a portion of one of the inner stent structure and outer stent structure within the hem.

4. The method of claim 2, wherein forming a hem on the mesh structure comprising attaching a hem to the mesh structure.

5. The method of claim 2, wherein forming a hem on the mesh structure comprising folding a portion of the mesh structure over itself.

6. The method of claim 1, wherein the tear drop shaped pores are arranged so that at least two of the tear drop shaped pores have enlarged rounded regions on a first end and smaller regions on a second end, and wherein enlarged rounded regions of at least two of the tear drop shaped pores are in contact with one another.

7. The method of claim 6, wherein a series of tear drop shaped pores extend along a long axis with the rounded region of a tear drop shaped pore being positioned along the axis at a first end and a pointed region of a tear drop shaped pore positioned along the axis on a second end, wherein the axis is straight.

* * * * *